United States Patent [19]

Vanheertum et al.

[11] Patent Number: 5,425,786
[45] Date of Patent: Jun. 20, 1995

[54] PROCESS FOR THE PRODUCTION OF SUSPENSIONS OF CYANURIC CHLORIDE IN AQUEOUS LIQUIDS

[75] Inventors: Rudolf Vanheertum, Ekeren; Richard Hendricx, Merksem; Norbert Kriebitzsch, Kapellen; Francois van de Velde, Merksem, all of Belgium; Ruediger Schirrmacher, Hanau, Germany

[73] Assignee: Dequssa Aktiengesellschaft, Frankfurt am Main, Germany

[21] Appl. No.: 119,880

[22] Filed: Sep. 13, 1993

[30] Foreign Application Priority Data

Sep. 25, 1992 [DE] Germany ............ 42 32 117.4

[51] Int. Cl.6 .............. B01J 13/00; C07D 251/28
[52] U.S. Cl. ................... 23/293 A; 544/190
[58] Field of Search ............ 23/293 A, 306; 544/190, 544/191

[56] References Cited

U.S. PATENT DOCUMENTS

| | | | |
|---|---|---|---|
| 4,017,413 | 4/1977 | Bittner et al. | 544/190 |
| 4,552,959 | 11/1985 | Punzar et al. | 544/190 |
| 4,656,272 | 4/1987 | Mortin et al. | 544/197 |
| 4,782,886 | 11/1988 | Uchida et al. | 164/305 |

FOREIGN PATENT DOCUMENTS

| | | |
|---|---|---|
| 0094665 | 4/1987 | European Pat. Off. . |
| 2162064 | 6/1973 | Germany . |
| 1670731 | 9/1977 | Germany . |
| 2850308 | 9/1984 | Germany . |
| 2850242 | 10/1984 | Germany . |
| 3524732 | 9/1986 | Germany ............ 544/190 |
| 2033898 | 5/1980 | United Kingdom ........ 544/191 |

*Primary Examiner*—John Zimmerman
*Assistant Examiner*—Stuart L. Hendrickson
*Attorney, Agent, or Firm*—Beveridge, DeGrandi, Weilacher & Young

[57] ABSTRACT

A process is described for the production of a suspension of cyanuric chloride in an aqueous liquid, more particularly, water. Molten cyanuric chloride is sprayed using a spray arrangement comprising a spray nozzle immersed in the aqueous liquid. Blockages in the nozzle during the critical start and stop phases are avoided by passing superheated steam through those parts of the spray arrangement which come into contact with the cyanuric chloride melt before and after the spraying process. A particularly reactive cyanuric chloride suspension is obtained by spraying a mixture of cyanuric chloride melt and superheated steam.

13 Claims, 4 Drawing Sheets

PROCESS FOR THE PRODUCTION OF SUSPENSIONS OF CYANURIC CHLORIDE IN AQUEOUS LIQUIDS

INTRODUCTION AND BACKGROUND

The present invention relates to a process for the production of suspensions of cyanuric chloride in aqueous liquids, more particularly water.

Cyanuric chloride is an important starting product for the manufacture of herbicides, optical brighteners, reactive dyes and plastic and rubber additives. These products are produced by substitution of the chlorine atoms of the cyanuric chloride by other ligands, for example those containing amine, mercapto or hydroxyfunctions. The reactions are well known in the art and are partly carried out in organic solvents, but to a large extent with suspensions of fine-particle cyanuric chloride in water or an aqueous organic reaction medium.

The aqueous cyanuric chloride suspensions can be obtained by converting the commercially available fine-particle cyanuric chloride powder into a paste in cold water with or without the assistance of wetting agents. Low temperatures slow down the unwanted hydrolysis reaction of the cyanuric chloride. The disadvantage of this method for producing suspensions of cyanuric chloride lies in the difficulties involved in handling bulk materials packed in 50 to 1,000 kg containers. Handling is complicated by the physiological and corrosive properties of the cyanuric chloride.

Accordingly, attempts have been made in the past to use cyanuric chloride in the form of a pumpable melt for the production of aqueous suspensions in the same way as can be done where certain organic solvents are used. To this end, the enthalpy of solidification and the specific heat have to be dissipated between the melting temperature and temperatures of preferably around 0° C. At the same time, the suspension formed must not reach temperatures at which the undesired hydrolysis reaction becomes too pronounced, in addition to which the cyanuric chloride particles have to be as small as possible to enable the subsequent synthesis to proceed quickly and selectively.

Prior art represented by German patent 16 70 731 and German published application 21 62 064 describe processes in which molten cyanuric chloride is sprayed into the vapor space of a stirred reactor partly filled with water. However, the effect of spraying molten cyanuric chloride into a gas space is that cyanuric chloride volatilizing from the melt desublimates in the gas space and forms crusts on the wall of the spray reactor which is not wetted with water. These crusts lead to blockages in the reactor and form lumps in the suspension.

German patents 28 50 242 and 28 50 308 describe a reactor which tapers downwards breast-fashion to an outflow opening and in which a spray nozzle is arranged in the reactor head. A rotating liquid ring is produced in the reactor, the cyanuric chloride melt being sprayed onto the surface of this liquid ring. To avoid caking, the rotational speed selected for the liquid ring is so high that the ring almost completely surrounds the spray nozzle at the cover of the reactor. In terms of control technology, this is difficult to guarantee on a permanent basis in the rough conditions of continuous operation. In addition, this construction provides for only a gradual improvement and, because the liquid ring has to be supported by a correspondingly narrow outflow opening, can only handle suspensions of relatively low concentration.

EP-B 0 094 665 describes a process for the production of a suspension of cyanuric chloride in water or for the reaction of cyanuric chloride in ammonia or amines which is said to avoid most of the disadvantages attending known processes. In this case, molten cyanuric chloride is sprayed into water or an aqueous ammonia or amine solution or suspension by means of a spray nozzle which dips into the liquid. Before the spraying process is started, however, the liquid level surrounding the nozzle is reduced to such an extent that the tip of the nozzle no longer dips into the liquid. The liquid level is only raised again after starting so that the nozzle dips into the liquid again. The above-mentioned problems characteristic of the spraying of molten cyanuric chloride into a gas space are not eliminated in this process either, particularly in the start and stop phases of the spraying process.

In all the processes mentioned above, the injection system, i.e. in particular, the spray nozzle and its feed pipe for molten cyanuric chloride, is prevented from being internally wetted with water during the start and stop phases because otherwise hydrolysis products would be formed from cyanuric chloride residues, blocking the nozzle and contaminating the cyanuric chloride suspension.

SUMMARY OF THE INVENTION

The object addressed by the present invention was to provide a process which would avoid the disadvantages of known processes during the start and stop phases and which would enable highly reactive aqueous cyanuric chloride suspensions to be produced.

The present invention therefore relates to a process for the production of a suspension of cyanuric chloride in an aqueous liquid, more particularly in water, the aqueous liquid optionally containing—in addition to water—dissolved organic solvents and/or reactants for the further reaction of the suspended cyanuric chloride formed. In carrying out the process molten cyanuric chloride is sprayed into the above-mentioned aqueous liquid during the process, which optionally already contains suspended cyanuric chloride, by using a spray arrangement comprising a spray nozzle which is always immersed in the aqueous liquid, even during the start and stop phases of the process. The temperature of the suspension is maintained in the range of 0° to 50° C. Superheated steam is passed through those parts of the spray arrangement which come into contact with molten cyanuric chloride immediately before and after the spraying process.

The key feature of the invention is that superheated steam is passed through the nozzle construction, which is permanently immersed in the liquid, during start and stop phases. The superheated steam has a temperature in the range from 150° to 300° C. and, more particularly, in the range from 200° to 290° C. It has been found that cyanuric chloride does not enter into hydrolysis reactions with superheated steam to any troublesome extent although it reacts very quickly and, in some cases, violently with liquid water at relatively high temperatures. Use is made of this knowledge in the respect that any water present in the nozzle or in the feed pipe is displaced by dry steam before the start phase and the cyanuric chloride melt is allowed to flow through immediately afterwards. In the stop phase, the reverse procedure is adopted so that the feed elements are freed from residual cyanuric chloride. At the same time, the introduction of steam supports the effect of the accompanying heating and insulation system arranged in known manner on the feed elements in the critical start and stop phases.

BRIEF DESCRIPTION OF DRAWINGS

Suitable arrangements for carrying out the process are illustrated in the accompanying drawings, wherein.

DETAILED DESCRIPTION OF THE INVENTION

Figure 1:
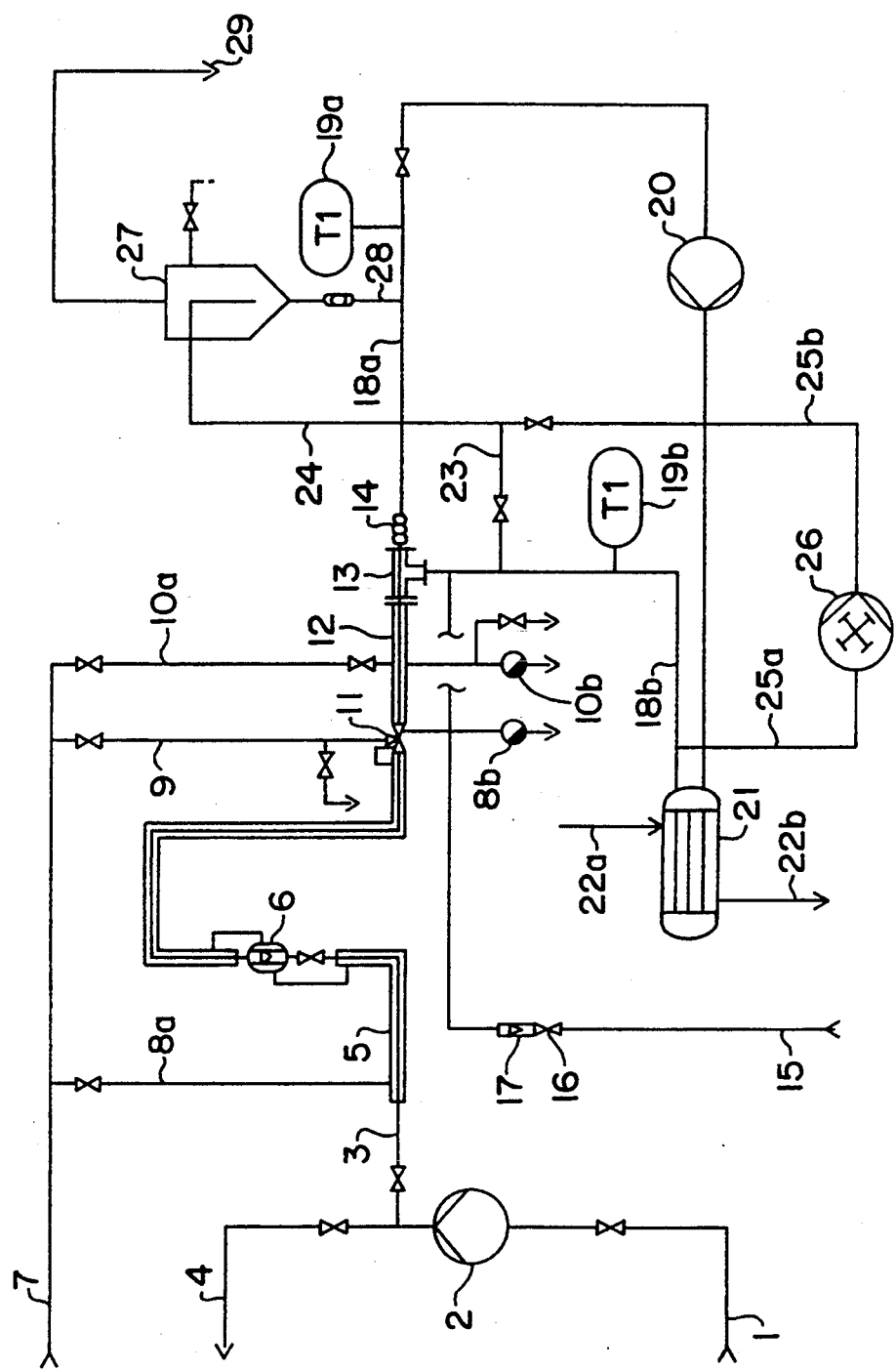
FIG. 1 diagrammatically illustrates a flow diagram of a plant for the production of cyanuric chloride suspensions.
Figure 2:
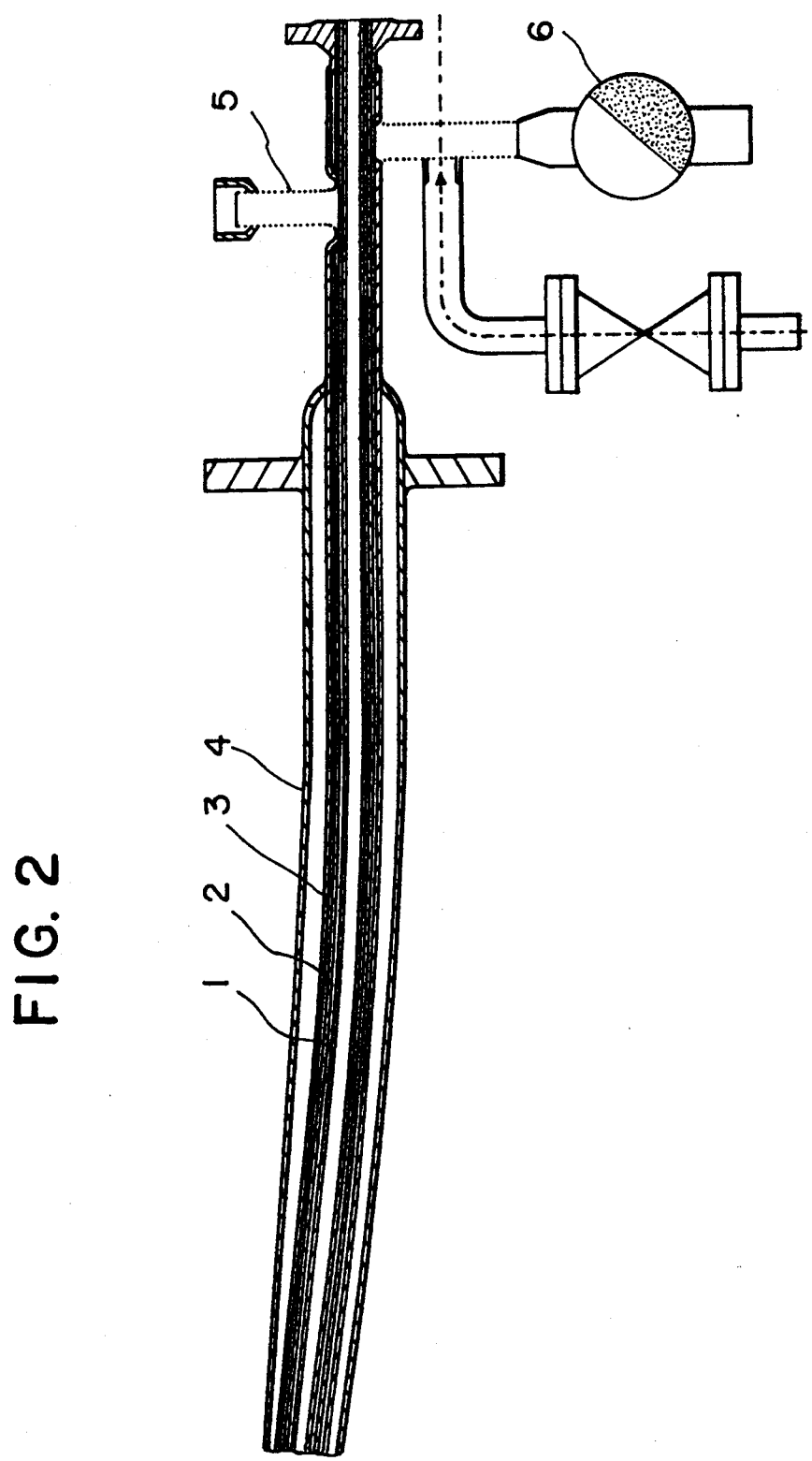
FIG. 2 is a longitudinal section through a steam-heated spray nozzle.
Figure 3:
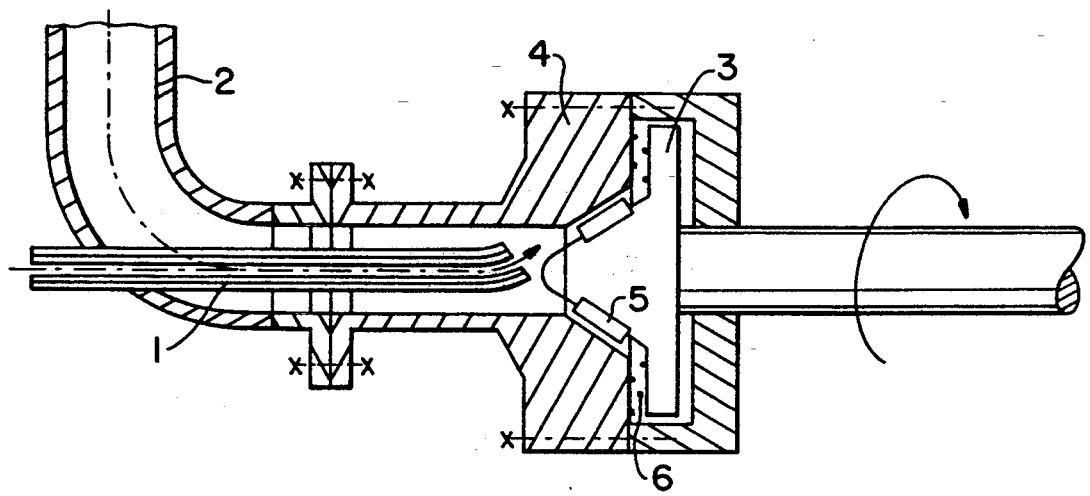
FIG. 3 is a longitudinal section through a spray arrangement with a facility for wet grinding immediately after formation of the suspension.

FIG. 1 diagrammatically illustrates a schematic flow diagram for a plant for carrying out the process according to the invention. Molten cyanuric chloride from a storage container (not shown) is delivered via a pipe 1, a pump 2 and a pipe 3 to the spray arrangement. Melt can be recycled through a pipe 4. The melt passes through the steam-heated pipe 5 with a control and measuring facility (control valve and rotameter) 6 for the volumetric flow rate to the three-way valve 11 and from there into the actual spray arrangement comprising the spray nozzle 12 and the chamber 13 for delivery of the aqueous liquid and formation of the suspension. The inspection window 14 is situated at the tip of the nozzle. Steam from pipe 7 is delivered through a pipe **8*a* for heating the pipe 5, the measuring and control unit 6 and the three-way valve 11. The condensate is removed through a condenser 8*b*. Steam is delivered to the heating jacket of the spray nozzle through the pipe 10*a*. Condensate is removed through the condenser 10*b*. Steam is delivered to the three-way valve 11 through the pipe 9 in order to free the nozzle 12 from cyanuric chloride before the start phase and after the stop phase. The pipes 18*a* and 18*b*, the pump 20, the cooler 21 (the references 22*a* and 22*b* denote the pipes through which the cooling medium is introduced and removed, respectively) and the chamber 13 form a suspension circuit to which water or a solids-free aqueous liquid is delivered through the pipe 15 equipped with a control valve 16 and a measuring instrument (rotameter) 17. The references 19*a* and 19*b* denote temperature measuring points before and after the cooler. Suspension from the suspension circuit mentioned is delivered to the tank 27 through the pipes 23 and 24 and returned via the pipe 28 to the pipe 18*a*. Suspension is removed through the pipe 29** and put to its intended use.

If required, a wet grinding facility may be integrated in the suspension circuit, all or part of the suspension being passed through the wet mill 26 and pipes **25*a* and 25*b***. If the suspension is to be concentrated, this may be done by means of a hydrocyclone (not shown).

The required particle fineness and, hence, the high reactivity of the cyanuric chloride in the suspension may be influenced through the outflow rate of the cyanuric chloride melt. The higher the outflow rate of the melt at the nozzle orifice or the smaller the nozzle opening, the finer the particles of suspended cyanuric chloride formed.

Typical one-component spray nozzles are suitable for the spraying process. A preferred one-component nozzle is shown in FIG. 2. Molten cyanuric chloride flows through the central pipe (1) of the nozzle. For heating, steam is introduced into the jacket pipe (2) through the connection (5). After the change in direction at the nozzle tip, steam and condensate flow through the jacket pipe (3) to the condensate drain (6). The jacket pipe (4) is an empty space for the thermal insulation of the nozzle.

Another preferred embodiment is characterized by the use of a spray arrangement comprising a two-component nozzle, the aqueous liquid surrounding the stream of molten cyanuric chloride guided centrally through the nozzle being delivered thereto by means of an annular gap situated at the nozzle orifice. The aqueous liquid may be the suspension itself, but is preferably a solids-free aqueous liquid, particularly fresh water, delivered to the system. The system pressure and the diameter of the nozzle are adapted to one another in such a way that the required outflow rate is obtained.

The cyanuric chloride melt to be sprayed generally has a temperature of 146° to 190° C. Providing the melt is under high pressure, it may even be sprayed at a temperature above 190° C.

In the context of the invention, the aqueous liquid in which the suspension is formed and, optionally, immediately further reacted is, in particular, water. It may also contain dissolved organic solvents, such as for example ketones, more particularly higher ketones which form an azeotrope with water. The aqueous liquid may also contain reaction components for the direct reaction of the cyanuric chloride particles formed during the spraying process. The reaction components in question are preferably ammonia or amines and, optionally, basic components for neutralizing the hydrochloric acid formed during the reaction.

Aqueous cyanuric chloride suspensions containing more than 50% by weight and preferably 20 to 50% by weight cyanuric chloride may be produced by the process according to the invention. The suspension is substantially free from hydrolysis products. The reactivity of the suspension formed may readily be determined in a test (see Example 2). The operating parameters for the spraying process required to obtain a certain reactivity may be adjusted on the basis of the test results obtained.

Provision does of course have to be made for the adequate dissipation of heat by cooling the suspension, for example by means of an internal and/or external coolers. The temperature of the suspension is generally kept between 0° and 30° C. and preferably below 20° C. during the spraying process. In one preferred embodiment of the process, the spraying arrangement comprising a nozzle with feed pipes for the cyanuric chloride melt and the dry steam is immersed in a spray reactor filled with the aqueous liquid. The contents of the reactor are circulated through an external intensive cooler. Fresh aqueous liquid is delivered to the circuit in a quantity commensurate with the quantity in which the cyanuric chloride suspension is removed and, if necessary, concentrated via a hydrocyclone.

If necessary, an apparatus for wet size reduction, for example a wet mill, may be integrated in the suspension circuit or in a sidestream thereof (as illustrated in FIG. 1). Any suitable wet grinding mill may be used for this purpose. In this case, the spray nozzle is positioned immediately in front of the suction side of the wet mill, as shown in FIG. 3, because it is possible in this way to obtain not only intensive suspension, but at the same time further minimization of the particle size of the cyanuric chloride and, hence, an increase in the reactivity of the particles. Thus FIG. 3, shows a lance-like steam-heated spray nozzle (same construction as in FIG. 2) for introduction of the cyanuric chloride melt, the feed pipe 2 for the aqueous liquid, the rotor 3 of the wet mill, the stator 4 of the wet mill, the blade-equipped rotating cone 5 and the fine size-reducing zone 6 (outlet pipe from the mill not shown).

It has also been found that particularly highly reactive cyanuric chloride suspensions are obtained if the cyanuric chloride melt is not sprayed by itself, but in admixture with superheated steam. The ratio by weight of steam to cyanuric chloride melt is 1:>2 and is preferably between 1:15 to 1:25. The mixture of cyanuric chloride and steam is best prepared immediately before spraying. Mixtures such as these may be prepared and immediately sprayed in two-component nozzles with an internal mixing zone.

Figure 4:
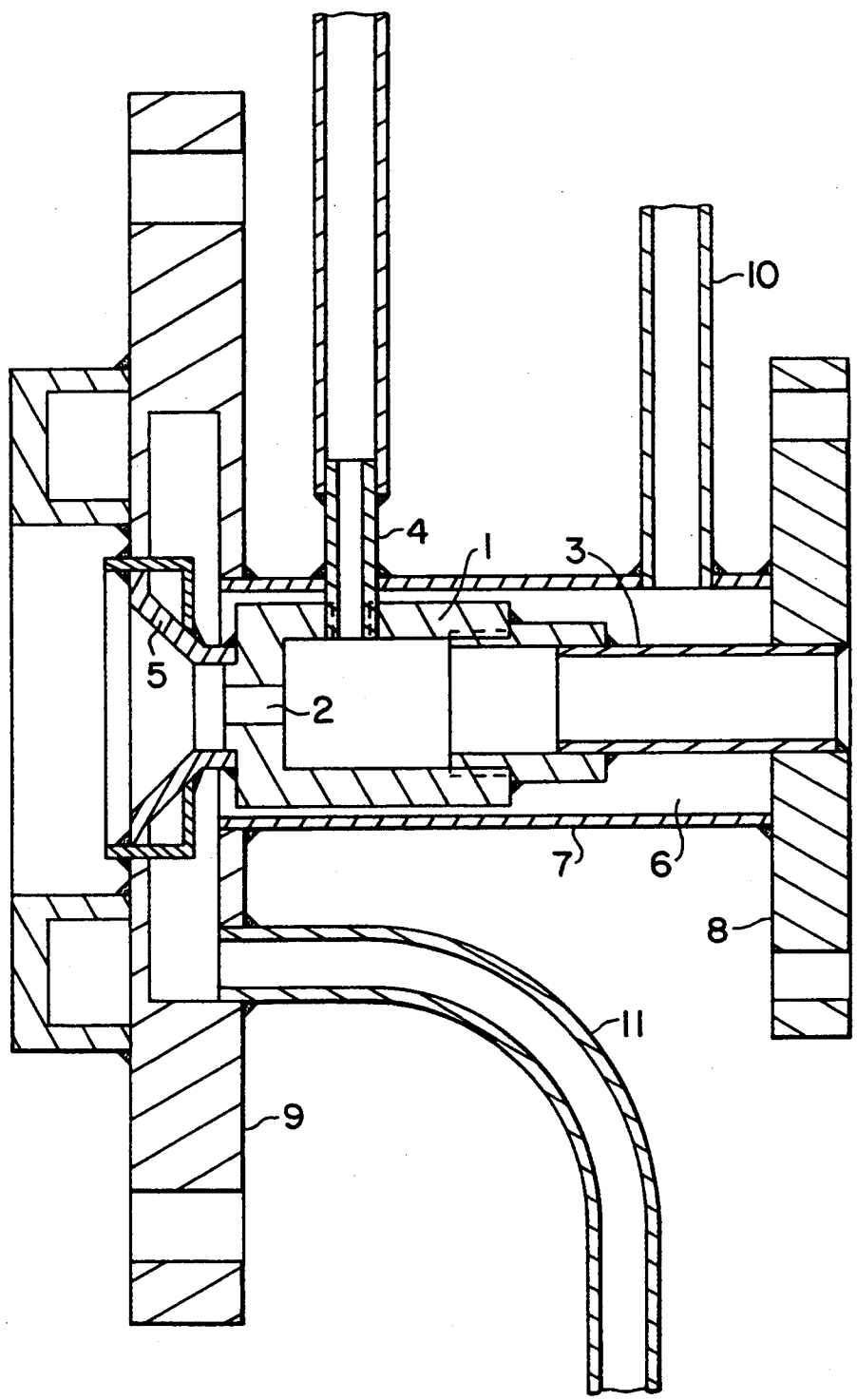
FIG. 4 is a cross-section through a spray arrangement for spraying a mixture of molten cyanuric chloride and steam.

A suitable nozzle construction is shown in FIG. 4. In the two-component nozzle illustrated, the actual nozzle body, consisting of the mixing chamber 1 with the nozzle orifice 2, the feed pipe 3 for cyanuric chloride melt, the feed pipe 4 for the steam to be added and the nozzle orifice 5, is surrounded by a steam-heated jacket space 6 formed from the pipe 7 and the end pieces 8 and 9. Steam for heating is delivered through the pipe 10 while condensate is removed through the pipe 11.

The different flow rates of the steam and the cyanuric chloride melt in one and the same nozzle produce pressure waves which cause the melt stream to break up into very fine floating droplets. Since the steam flowing out in the mixture condenses in the aqueous liquid, there are none of the gas loads which would occur if purging gases, such as hot nitrogen for example, were used. In addition, no third and possibly troublesome substance is introduced by steam. By spraying the mixture of molten cyanuric chloride and steam, it is possible to obtain high outflow rates despite a low system pressure and/or a wide nozzle orifice. Blockages in the nozzle are completely avoided in this way.

The advantages afforded by the invention are that the problems hitherto unavoidable in the start and stop phases of the spraying process can be eliminated. Malfunctions attributable to blockages in the spray arrangement are avoided. Accordingly, even small production batches can be sprayed. According to the invention, reactivity can be further increased not only through the possibilities known per se for controlling the particle size and hence the reactivity of the suspended cyanuric chloride particles through the pressure in the nozzle, the construction of the nozzle and the diameter of the nozzle, but also by the fact that a mixture of cyanuric chloride and steam is sprayed. The increase in reactivity leads to shorter reaction times during the subsequent reaction of the suspension with reactants.

EXAMPLE 1

Before the beginning of the test, the pipes and those parts of the plant which come into contact with the cyanuric chloride melt are preheated with steam (12bar/270° C.). Fresh water is introduced into the suspension circuit (as in FIG. 1, but with no wet mill) comprising a one-component spray nozzle (12), means (13) for surrounding the melt stream with the aqueous liquid, a pump (20), a cooler (21) and a circulation pipe (18) connecting these units. 5 m³/hour water are circulated. Steam (12bar/270° C.) is delivered to the cyanuric chloride nozzle (12) through the three-way valve (11). After 30 seconds, the three-way valve is reversed. In this way, liquid cyanuric chloride is introduced into the nozzle instead of steam. The fresh water supply (15) is also opened. A fine-particle suspension—visible through the inspection window (14)—immediately appears at the outlet opening of the nozzle which is immersed in the water circuit. The throughput of cyanuric chloride is adjusted to 970 kg/hour and the throughput of water to 3,900 kg/hour. Accordingly, cyanuric chloride issues from the nozzle (4 mm diameter orifice) at a rate of 14.8 m/s. The temperature is kept at 16° C. The concentration of the suspension removed from the circuit is 20% by weight. An average particle size of 29 μm is determined by laser diffraction. The plant is operated for another 12 minutes. During the stop phase, the three-way valve is reversed and the nozzle is briefly purged with steam.

EXAMPLE 2

1,490 kg/hour fresh water and 990 kg/hour molten cyanuric chloride are introduced into the plant described in Example 1. For the start phase, the cyanuric chloride nozzle is purged with 12 bar steam for 30 seconds before addition of the cyanuric chloride is commenced. After addition of the molten cyanuric chloride has been commenced, the temperature of the suspension is kept at 20° C. throughout the 12-minute test period. A suspension of 40% cyanuric chloride in water is obtained. The average particle size of the cyanuric chloride particles is 30 μm. The hydrolysis of the suspended cyanuric chloride at the point (29) where it is removed from the plant is negligible. During the stop phase, the nozzle is briefly purged with steam.

The 40% by weight suspension of cyanuric chloride in water obtained in this way is tested for its reactivity in known manner by reaction with sodium hydrogen sulfide to tris-mercapto-s-triazine. To this end, the reaction is carried out once with the suspension prepared in accordance with the invention and once as a blank test with freshly suspended powder-form cyanuric chloride having an average particle diameter of 33 μm.

281 g 37.8% NaSH and 12 g 50% NaOH are introduced into a 1 liter laboratory reactor equipped with a stirrer, a double jacket for cooling, a thermometer and an inlet funnel. 269 g 40% by weight cyanuric chloride suspension and 88 g 50% NaOH are added at a temperature kept at 50° to 60° C. After a reaction time of 1 hour at 50° C., the quantitative conversion of the cyanuric chloride was verified by thin-layer chromatography in both tests.

After addition of another 54 g 50% NaOH and an after-reaction time of 30 minutes at 50° C., the reaction mixture was cooled to 10° C. and the tris-mercapto-s-triazine trisodium salt was filtered off. 253 g filter cake were obtained. In both cases, the product obtained had a high degree of crystallinity and showed the same content in HPLC analysis.

EXAMPLE 3

The procedure is the same as in Example 2 except that 1500 kg/hour of a 10% by weight solution of acetone in water are passed through as the aqueous liquid together with 990 kg/hour molten cyanuric chloride.

The 40% by weight suspension obtained has an average particle size of 28 μm.

EXAMPLE 4

For this test, the plant described in Example 1 is equipped with the two-component nozzle shown in FIG. 4 instead of the one-component nozzle used in Example 1. The cyanuric chloride pipe and the nozzle are preheated with steam (12 bar/270° C.). The suspension circuit is filled with fresh water and circulated (5 m³/hour). The outlet orifice of the nozzle is 4.2 mm in diameter. Steam (12 bar/270° C.) is delivered in a quantity of 16 kg/hour to the two-component nozzle via a throughflow meter and the steam connection ((3) in FIG. 3). 344 kg/hour molten cyanuric chloride are then introduced into the two-component nozzle. 2,060 kg/hour fresh water are introduced into the circuit and 2,420 kg/hour suspension are removed. Steam and molten cyanuric chloride are continuously delivered to the two-component nozzle throughout the test. The steam immediately condenses at the outlet point which is submerged in the circulating liquid. The concentration of the suspension obtained is 14% and the average particle size 30 μm. The test is terminated after 8 minutes by shutting off first the supply of cyanuric chloride and then the supply of steam.

Further modifications and variations, of the foregoing will be apparent to those skilled in the art and are intended to be encompassed by the claims appended hereto.

German priority document P42 32 117.4 and incorporated herein by reference.

We claim:

1. A process for the production of a suspension of cyanuric chloride in an aqueous liquid comprising spraying molten cyanuric chloride in the form of a mixture of molten cyanuric chloride and superheated steam into said aqueous liquid by using a spray nozzle immersed in said aqueous liquid, maintaining a temperature of 0° to 50° C. in said liquid, and passing superheated steam through those parts of the spray nozzle means which come into contact with molten cyanuric chloride.

2. The process according to claim 1 wherein the aqueous liquid is water.

3. The process according to claim 1 wherein the aqueous liquid comprises water, dissolved organic solvents.

4. The process according to claim 1 wherein the aqueous liquid into which the molten cyanuric chloride is sprayed contains suspended cyanuric chloride.

5. The process according to claim 1, wherein mixture is prepared and immediately sprayed in a two-component nozzle means with an internal mixing zone.

6. The process according to claim 1, wherein superheated steam and molten cyanuric chloride are mixed in a ratio by weight of 1:15 to 1:25.

7. The process according to claim 1, wherein said molten cyanuric chloride is sprayed in the form of a melt stream substantially surrounded by said aqueous liquid.

8. The process according to claim 7, wherein a spray arrangement comprising a two-component nozzle, the aqueous liquid surrounding the cyanuric chloride melt stream guided centrally in the nozzle being delivered thereto by means of an annular gap situated at the nozzle orifice.

9. The process according to claim 1 wherein the nozzle orifice of the spray arrangement is arranged immediately in front of the suction side of a wet grinder.

10. The process according to claim 1 wherein the spray nozzle is purged with superheated steam before said spraying.

11. The process according to claim 1 wherein the spray nozzle is purged with superheated steam after spraying is ceased.

12. A process for the production of a suspension of cyanuric chlorine in an aqueous liquid comprising spraying molten cyanuric chloride in the form of a mixture of molten cyanuric chloride and superheated steam into said aqueous liquid by using a spray nozzle immersed in said aqueous liquid and maintaining a temperature of 0° to 50° C. in said liquid, wherein thereafter purging said nozzle with steam after spraying is completed.

13. The process for the production of a suspension of cyanuric chlorine in an aqueous liquid comprising spraying molten cyanuric chloride in the form of a mixture of molten cyanuric chloride and superheated steam into said aqueous liquid by using a spray nozzle immersed in said aqueous liquid and maintaining a temperature of 0° to 50° C. in said liquid, wherein said nozzle is purged with steam immediately before spraying.

* * * * *